United States Patent [19]

Stiefel

[11] Patent Number: 5,072,056

[45] Date of Patent: Dec. 10, 1991

[54] SYNTHESIS OF 2-PHENYL-1,3-PROPANEDIOL

[75] Inventor: Frank J. Stiefel, Princeton Junction, N.J.

[73] Assignee: Carter-Wallace, Inc., New York, N.Y.

[21] Appl. No.: 412,769

[22] Filed: Sep. 26, 1989

[51] Int. Cl.$^5$ ..................... C07C 27/04; C07C 29/132
[52] U.S. Cl. .................... 568/814; 560/164; 564/259; 568/811
[58] Field of Search ............... 568/705, 811, 927, 814; 564/259; 560/164

[56] References Cited

U.S. PATENT DOCUMENTS

| | | | |
|---|---|---|---|
| 2,884,444 | 4/1959 | Berger et al. | 560/164 |
| 4,482,760 | 11/1984 | Kleemann et al. | 568/811 |
| 4,868,327 | 9/1989 | Stiefel | 568/811 |

*Primary Examiner*—Werren B. Lone
*Attorney, Agent, or Firm*—Kevin B. Clark

[57] ABSTRACT

A novel method of preparing 2-phenyl substituted-1, 3-propanediols, useful intermediates in the synthesis of pharmaceutical preparations is disclosed.

6 Claims, No Drawings

SYNTHESIS OF 2-PHENYL-1,3-PROPANEDIOL

This invention relates to a novel method for the synthesis of 2-phenyl substituted-1,3-propanediols.

The synthesis of 2-phenyl-1,3-propanediol has, in the past, been carried out in accordance with the procedures such as those described in U.S. Pat. No. 2,884,444.

The principal drawbacks associated with the synthesis disclosed in the prior art are:

The starting materials employed in the synthesis, 2-phenyl substituted-1,3-propanediols are obtained by the lithium aluminum hydride reduction of diethyl phenyl substituted malonates. The diethyl phenyl substituted malonates are relatively expensive materials and the lithium aluminum hydride reduction procedure is costly, hazardous and not desirable for the production of large quantities of materials.

It has now been found that the hereinafter disclosed route to 2-phenyl substituted-1,3-propanediols is an economical and less hazardous procedure than those presently available which readily lends itself to commercial operation. As used hereafter, the term phenyl substituted shall include halogen, aliphatic, trifluoro methyl hydroxyl, methoxy, alkoxy and the like substituents.

Example 1 describes the preparation of phenyl substituted nitromethylbenzene by oxidation of a corresponding phenyl substituted benzaldehyde oximes under controlled conditions.

This procedure involves the oxidation of phenyl substituted benzaldehyde oximes to the corresponding phenyl substituted nitro methyl benzenes using peracetic acid and its reaction with formaldehyde to form stable 2-phenyl substituted 2-nitro-1,3-propanediols.

It has been proposed previously to prepare such phenyl substituted nitromethylbenzene by reacting benzylhalide with silver nitrite or sodium nitrite in dimethyl sulfoxide. Such procedures are expensive, give relatively low yields as well as low purity of product. Moreover, the use of dimethyl sulfoxide presents environmental problems. Further, it has been proposed to prepare nitromethylbenzene by the oxidation of benzaldehyde oxime with trifluroacetic acid and a phosphate buffer. This procedure is also expensive and gives low yields.

In accordance with the present invention, the oxidation of benzaldehyde oxime is accomplished by using either 30% or 50% hydrogen peroxide or preferably commercial 35% peracetic in acetic acid as an oxidizing agent at controlled temperatures of from about 80° C. to about 90° C. to obtain high yields of high purity phenyl substituted nitromethylbenzene.

Example 2 describes the further reaction of phenyl substituted nitromethylbenzenes with formaldehyde to obtain 2-nitro-2-phenyl-1,3-propanediol.

The literature preparation of nitrodiols involves the reaction of nitromethylbenzene with formaldehyde, however, in accordance with the present invention, the reaction has been modified whereby a base such as sodium bicarbonate, sodium carbonate monohydrate or sodium carbonate is used as the catalyst in lieu of the previously preferred sodium hydroxide. This change in catalyst has been found to allow a more controlled addition of the nitro compound to the formaldehyde with a lessening in the amount of polymeric materials formed in side reactions.

As more particularly described in Example 3, the materials are reduced with a suitable catalyst and hydrogen to remove the nitro group and provide the pharmaceutically useful 2-phenyl substituted-1,3-propanediols.

In the past, the removal of an aliphatic nitro group from a molecule have included reacting a tertiary nitro compound with tributyltinhydride. The latter reagent is very costly and not conducive to large scale production. Another method proposed is the hydrogenation of a benzylnitro compound with palladium on charcoal at 1200 psi. Debenzylation occurs however, no yield information is available when the reaction was carried out at 1200 psi. When the reaction was carried out at 50 psi, using palladium on charcoal, a mixture containing debenzylated and amino compounds was formed in quantities which preclude the commercial adaptation of the reaction. In accordance with the present invention, it has been discovered that the removal of the aliphatic nitro group may be carried out by the hydrogenation of 2-nitro-2-phenyl-1,3-propanediol in the presence of palladium on calcium carbonate at 50 psi. The procedure permits the production 2-phenyl-1,3-propanediol of high purity in yields of about 80%. The method allows for large scale hydrogenation in standard reactors, capable of sustaining 125 psi.

The method of the present invention is quantitative and precludes contamination of the final product. Moreover, the synthesis is readily adaptable to commercial scale since the chlorocarbonate solution is easily pumped into ammonium hydroxide and removal of the organic solvents easily accomplished by distillation under reduced pressure.

To describe the synthesis of the present invention more particularly, the following non-limiting examples will serve to illustrate the novel synthesis in its preferred embodiments.

EXAMPLE 1

Nitromethylbenzene 184.1 g. (1.51 mole) of benzaldehyde oxime and 185 ml. of glacial acetic acid are placed in a 3 liter 3 neck flask. The mixture is stirred and heated to 80° C. A solution of 344.1 g. (1.65 mole) of 36.6% peracetic acid and 19 g. of sodium acetate trihydrate is added at a rate such that the temperature is maintained between about 80° and about 90° C. Stirring is continued at about 85° C. for about 3 ½ hours until there is no oxime. The reaction mixture is chilled to 25° C. and one liter of water is added and the mixture stirred well and the oil which forms, is separated. The aqueous layer is extracted twice with 200 ml. of methylene chloride. The aqueous extract is combined with the oil layer and washed twice with 600 ml. of water and once with 600 ml. of 5% sodium bicarbonate solution, washed again with 400 ml. of water, and dried over sodium sulfate and concentrated to a light orange oil. The yield is 173.5 g. (84%) of 97% pure material by GC.

EXAMPLE 2

2-Nitro-2 Phenyl-1.3-Propanediol 100 g. (0.73 mole) of nitromethylbenzene, 131.5 g. (1.61 mole) of 37% formaldehyde and 1.8 g. of sodium carbonate monohydrate are placed in a 500 ml. beaker equipped with a mechanical stirrer. The mixture is stirred, the temperature rises to 38° C. and is maintained at 38° C. by using a cold water bath. After 1 ½ hours, crystals begin to form. The mixture is diluted with 210 ml. of ice water and stirred at 10° C. for about 2 hours. The mixture is filtered and the filtrate washed with water. The damp cake is placed back in the beaker and 280 ml. of ice water is added. The mixture is stirred for 1 hour, filtered and air dried overnight. The solid is stirred with 250 ml. of toluene for about 1 hour at 10° C. and filtered, then washed with cold toluene and dried. The yield is 112.6 g. of nitrophenyldiol (78%), M.P. 96°-97.5° C.

EXAMPLE 3

2-Phenyl-1.3-Propanediol 12 g. (0.06 mole) of 2-nitro-2-phenyl-1,3-propanediol, 400 mg. of 5% palladium on calcium carbonate and 150 ml. of methanol are placed in a Parr hydrogenator bottle and reduced with hydrogen overnight. The mixture is filtered through Celite, concentrated to an oil and recrystallized from 30 ml. of toluene. The yield is 7.4 g. (80%) of product, M.P. 52°-4° C.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for preparing 2-phenyl substituted-1, 3-propanediols selected from the group consisting of halogen, aliphatic, trifluoromethyl hydroxyl, methoxy, and alkoxy phenyl substituted diols which comprises the steps of:
   a) oxidizing a phenyl substituted benzaldehyde oxime at controlled temperatures of from about 80° C. to about 90° C. with an oxidizing agent selected from the group consisting of 30% hydrogen peroxide, 50% hydrogen peroxide or 35% peracetic acid in acetic acid to obtain the corresponding phenyl substituted nitromethylbenzene;
   b) reacting the phenyl substituted nitromethylbenzene obtained in step a) with formaldehyde and a base selected from sodium carbonate, sodium carbonate monohydrate or sodium bicarbonate while maintaining the reaction temperature at or below about 38° C. to form a 2-nitro-2-phenyl substituted-1,3-propanediol;
   c) reducing a 2-nitro-2-phenyl substituted-1,3-propanediol obtained in step b) with hydrogen in the presence of a palladium on calcium carbonate catalyst to form a 2-phenyl substituted-1,3-propanediol.

2. A method according to claim 1, step a, wherein said compound is hydroxylamine sulfate.

3. A method according to claim 1, step a, wherein aid compound is hydroxylamine hydrochloride.

4. A method according to claim 1, step b, wherein said oxidizing agent is peracetic acid.

5. A method according to claim 1, step c, wherein said base is sodium carbonate monohydrate.

6. A method according to claim 1, step d, wherein the reduction of the 2 nitro-2-phenyl substituted-1,3-propanediol is carried out at 50 psi.

* * * * *